comparative polymer and that the water absorption of the copolymer of Example 3 was 0.39% lower than that of comparative polymer C.

EXAMPLE 4

45/45/10 Molar Hydroquinone/4,4'-Dihydroxydiphenyl Sulfone (4,4'-Bisphenol S)/DTBHQ-Dichloro-Diphenylsulfone Terpolymer In an apparatus similar to that of Example 1 were placed:
21.30 g ( 85.1 mmole) Bisphenol S,
9.38 g ( 85.2 mmole) Hydroquinone,
4.21 g ( 18.9 mmole) 2,5-di-t-butylhydroquinone,
54.56 g (190.0 mmole) 4,4'-dichlorodiphenylsulfone,
27.05 g (195.7 mmole) anhydrous potassium carbonate,
177 g sulfolane, and
76 g chlorobenzene.

The mixture was heated under nitrogen, distillation of chlorobenzene and water beginning at 166° C. Dropwise addition of chlorobenzene was started at 220° C., and the temperature was maintained at 230°–235° C. for 6 hours. The polymer was endcapped and recovered essentially as described in Example 1. Yield: 53.46 g (70.7%), reduced viscosity (measured in N-methylpyrrolidone, concentration 1.0 g/dl, at 25° C.), 0.68 dl/g. Properties of compression molded plaques are shown in Table 1.

COMPARATIVE EXAMPLE D

50/50 Hydroquinone/4,4'-Bisphenol S-Dichlorodiphenylsulfone Copolymer

This copolymer was prepared by a method entirely analogous to that of Example 4 except that the heating time at 229°–235° C. was 5 hours. Yield: 52.85 g (68.8%), reduced viscosity (in N-methylpyrrolidone, 1.0 g/dl, at 25° C.), 0.69 dl/g. Properties of the terpolymer of Example 4 and the copolymer of Comparative Example D are shown in Table 2. The glass transition temperature of the terpolymer was 5° C. higher, and its water absorption was 3% lower.

EXAMPLE 5

51/34/15 Molar 4,4'-Biphenol/Bisphenol A/DTBHQ-Dichlorodiphenylsulfone Terpolymer In an apparatus similar to that of Example 1 were placed the following materials:
13.96 g ( 61.2 mmole) bisphenol A,
51.39 g (179.0 mmole) 4,4'-dichlorodiphenyl sulfone,
29.68 g (214.8 mmole) anhydrous potassium carbonate,
160 g distilled sulfolane, and
160 g chlorobenzene.

The mixture was heated in a nitrogen, atmosphere; at 147° C. distillation of chlorobenzene and water began. The mixture was stirred for 1 hour at 170° C. while chorobenzene was being added dropwise. The temperature was lowered somewhat, chlorobenzene addition was stopped, and 4,4'-biphenol (17.08 g, 91.7 mmole) and DTBHQ (6.00 g, 27.0 mmole) were added and rinsed into the reactor with a total of about 10 ml of chlorobenzene. The mixture was heated to 220° C., chlorobenzene addition was resumed, and reaction was continued at 220°–221° C. for about 4.8 hours. The terpolymer was endcapped and recovered essentially as described in Example 1. Yield: 53.30 g (70.7%), reduced viscosity (in N- methylpyrrolidone, 1.0 g/dl at 25° C.) 1.10 dl/g. Properties of compression molded plaques of the terpolymer are given in Table 1.

COMPARATIVE EXAMPLE E

60/40 Molar 4,4'-Biphenol/Bisphenol A-Dichlorodiphenylsulfone Copolymer

Copolymers of this composition could be made by methods as described in Example 5. It was found that both the glass transition temperature and the water absorption were affected by changes in the molecular weight of the copolymer. Therefore, in Table 2 ranges for both of these properties are given. In all cases, the terpolymer of Example 5 had a higher glass transition temperature and an equal or lower water absorption.

EXAMPLE 6

Polymer from DTBHQ and 4,4'-Dichlorodiphenylsulfone

In an apparatus similar to that used for Example 1, were placed the following materials:
28.01 g (126.0 mmole) of 2,6-di-t-butylhydroquinone
36.18 g (126.0 mmole) of 4,4'-dichlorodiphenylsulfone
141.0 g of diphenylsulfone, and
83.0 g of chlorobenzene.

The mixture was heated under a nitrogen atomsphere. When the temperature reached 134° C. and the diphenylsulfone was melted, the heat source was removed and anhydrous potassium carbonate (20.89 g, 151.2 mmole) was added and rinsed into the flask with a small amount of chlorobenzene. Heating was resumed, and chlorobenzene and water began to distill off at 158° C. The reaction mixture was heated at 280° C. for about 7 hours and then was poured into a metal pan and allowed to solidify. The crude product was reduced mechanically to a fine powder and then washed successively with boiling acetone (two portions), deionized water, hot 0.7 percent hydrochloric acid, and boiling methanol. The yield of polymer after drying in a vacuum oven at 150° C. was 43.36 g (78.8 percent).

DSC investigation of the polymer indicated a melting point of 387° C. (just heating cycle) and 383° C. (second heating cycle). The Tg was estimated to be about 225°–230° C.

TABLE 1

| | Example No: | | | | | |
| --- | --- | --- | --- | --- | --- | --- |
| | 1 | 2 | 3 | 4 | 5 | 6 |
| Copolymer Composition, Mole % | | | | | | |
| DTBHQ* | 50 | 60 | 21 | 10 | 15 | 100 |
| 4,4'-Biphenol | 50 | — | — | — | 51 | — |
| Bisphenol A | — | 40 | — | — | 34 | — |
| Bisphenol | — | — | 79 | 45 | — | — |
| Hydroquinone | — | — | — | 45 | — | — |
| DCDPS | 100 | 100 | 100 | 100 | 100 | 100 |
| Physical Properties | | | | | | |
| $T_g$, °C. | 225 | 220 | 235 | 220 | 215 | 225–230** |
| Tensile Modulus psi | 225,000 | 256,000 | 272,000 | 250,000 | 241,000 | — |

OTHER PUBLICATIONS

Chemical Abstracts, vol. 66, Abst No. 114184f, 1967.
Chemical Abstracts, vol. 77, Abst. No. 3653r, p. 401A, Abst. No. V12603, 1978.
Zarling et al., J. Cell. Biol., Vol. 79, 2 part 2, p. 401A, 1978.
Muramatsu, T. et al., J. Biochem., vol. 89, pp. 473–481, 1981.
Prujansky–Jacobovits, A. et al., Biochem. Biophys. Res. Comm., vol. 89, pp. 448–455, 1979.
Muramatsu, T. et al., Biochem. Biophys. Res. Comm., vol. 96, pp. 1547–1553, 1980.
Pearlstein, E., Exper. Cell. Res., vol. 109, pp. 95–103, 1977.
Muramatsu, T. et al., Cell, vol. 18, pp. 183–191, 1979.
Symes et al., Br. J. Cancer, vol. 28, Suppl I, pp. 276–284, 1973.

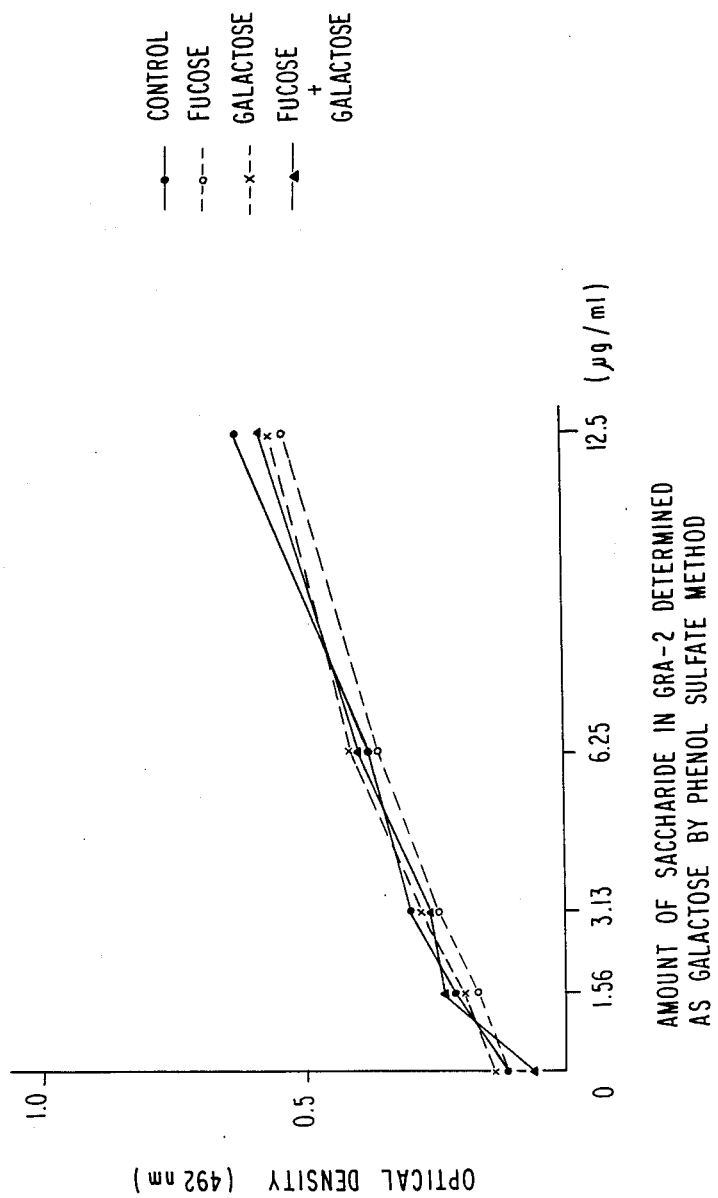

PROCESS FOR PREPARING GLYCOSIDIC LINKAGE RELATED ANTIGEN

FIELD OF THE INVENTION

The present invention relates to a novel process for preparing glycosidic linkage related antigen derived from cancer cells (hereinafter referred to as "GRA").

BACKGROUND OF THE INVENTION

As described in GB No. 2106935A corresponding to Japanese Patent Application (OPI) No. 1420/84 it is known that GRA is a component of the membrane of a cancer cell, which can bind a lectin capable of binding a terminal galactose and/or terminal N-acetyl galactosamine, acts as an immunogen for the host and has very high immunogenicity that causes an immune response specific to the cancer cells and that this exhibits an excellent effect in the therapy and prophylaxis of cancer.

SUMMARY OF THE INVENTION

Extensive research has been made under such technical environment, and as a result, it has been found that an epitope which can be recognized by a monoclonal antibody GGF described hereinbelow is present in the specific glycosidic linkage structure of the above-described GRA, and it has also been found that a GRA can be obtained efficiently using means for isolation making use of affinity for said terminal fucose glycosidic linkage structure.

Therefore, the present invention provides a novel process for preparing a GRA from a cancer cell membrane component making use of affinity for a terminal fucose glycosidic linkage.

BRIEF DESCRIPTION OF THE DRAWINGS

The FIGURE is a graph showing the influence of the addition of a monosaccharide on the first reaction of lectin-GGF antibody binding assay, i.e., the reaction between GGF antibody and GRA-2.

DETAILED DESCRIPTION OF THE INVENTION

The process of the present invention can be carried out using conventional physico-chemical or biochemical techniques making use of affinity for a terminal fucose glycosidic linkage. More particularly, it can be performed by treating a cancer cell membrane component with a substance having affinity for a terminal fucose glycosidic linkage structure to bind GRA thereto and then releasing the GRA therefrom.

Various techniques can be used as such means. Examples of such techniques include not only common techniques such as affinity chromatography and immune precipitation but also generally used purifying techniques such as gel filtration, electrophoresis, dialysis and physical precipitation using a glycoprotein precipitating agent, e.g., polyethylene glycol and acetone, and combinations thereof.

Cancer cell membrane components to be used as raw materials in the present invention are not specifically limited, and any and every one may be used, prepared according to conventional means from human or animal cancer cells such as cultured cancer cells, transplanted cancer cells, spontaneous cancer cells, chemical or virus induced cancer cells, and cancer cells derived from operated tissues. Separation of cancer cell membrane component can be carried out by known methods, such as homogenizing method, or solubilizing method using a solubilizing agent. Preferably, it can be carried out by a method which comprises homogenizing cancer cells in physiological saline or in a suitable buffer solution, separating the formed precipitate by centrifugal separation, etc., dissolving it in physiological saline or in a buffer solution in the presence of a solubilizing agent, and separating the supernatant by centrifugal separation, etc. Various surface active agents which are known to solubilize cell membranes can be used as the solubilizing agent. Examples thereof include nonionic surface active agents such as "Triton X-100" (produced by Wako Pure Chemical Industries, Ltd.), "NP-40" (produced by Shell Co.), digitonin or urea, etc. and anionic surface active agents such as sodium dodecyl sulfate (SDS), etc.

The process of the present invention will now be explained in greater detail in the following, taking an example of an embodiment in which affinity chromatography is used.

A column carrier to be used in said chromatography can easily be obtained by fixing a substance capable of binding a terminal fucose on an insoluble support. Said substances capable of binding a terminal fucose include, for example, fucose-binding lectins such as *Lotus tetragonolobus*-lectin (*Brt. J. Exp. Pathol,* 34, 94 (1953)), *Ulex europeus*-lectin (*Blood,* 9, 1195 (1954), etc.; and fucose-binding antibodies such as SSEA-1 (*Biochem. Biophys. Res. Commun.,* 100, 1578–1586 (1981)), ZWG 29, 13, 14, 111 (*Arch. Biochem. Biophys.* 217, 647–651 (1982)), 538F12, F8 (*Arch. Biochem. Biophys.* 220, 318–320 (1983)), VEP 8, 9 (*Eur. J. Immunol.* 13, 306–312 (1983)), My-1 (*Blood,* 61, 1020–1023 (1983)), GGF, etc. Among them are preferred such substances as having an affinity for a glycosidic linkage structure III$^3$V$^3$Fuc$_2$nLc$_6$ described in *Biochem. Biophys. Res. Commun.,* 109 (1) p. 36–44 (1982) (difucosyl glycosidic linkage structure), e.g., the GGF-antibody as prepared according to the reference example as given hereinbelow.

The GGF antibody is a monoclonal antibody which is characterized by its reactivity to III$^3$V$^3$Fuc$_2$nLc$_6$ and III$^3$V$^3$VII$^3$Fuc$_3$nLc$_8$ but not to III$^3$FucnLc$_4$. The antibody having such unique activity to glycosidic linkage is new and has been prepared by the present inventors for the first time.

The fixation (immobilization) of the abovementioned terminal fucose-binding substance on the insoluble support can be carried out by the known methods of fixing the living matters. Among them, it is preferred to use fixation by a method using a polysaccharide activated with cyanogen bromide and a method using N-hydroxysuccinimide ester. The method using a polysaccharide activated with cyanogen bromide comprises treating an insoluble support with cyanogen bromide and coupling the resultant activated materials with the terminal fucose-binding substance under mild conditions to fix said substance to the support. In carrying out treatment of the insoluble support with cyanogen bromide, the support may be treated in water or acetonitrile at room temperature with keeping the pH at 7.5 to 12 with a basic compound such as sodium hydroxide or sodium hydrogen carbonate, etc. or in a buffer solution having a pH of 7.5 to 12 such as a 0.1M sodium hydrogen carbonate solution having a pH of about 8.7 or a 0.01M phosphoric acid buffer solution having a pH of about 7.7, etc. for about 1 to 12 minutes. The amount of the cyanogen bromide used in generally nearly the same weight as that of the insoluble support. As the insoluble support, it is possible to use any known insoluble supports that show a low non-specific adsorption to living matters in general and have a high porosity, which have a functional group capable of fixing the living matters under mild conditions and are sufficiently stabilized chemically and physically. Examples of insoluble support include cellulose supports such as aminoethyl cellulose, carboxymethyl cellulose, bromoacetyl cellulose or p-anilino cellulose, etc., crosslinked dextran supports such as Sephadex or CM-Sephadex (produced by Pharmacia Co.), etc. and agarose supports such as Sepharose 2B, Sepharose 4B or Sepharose 6B (produced by Pharmacia Co.), etc. In case of carrying out coupling of the resultant support activated with cyanogen bromide with the terminal fucose-binding substance, the support activated with cyanogen bromide is used in an amount of 30 to 80 times by weight of that of said substance, and the reaction is carried out generally at 0 to 40° C., preferably 2° to 8° C. for about 10 to 20 hours in a suitable solvent, for example, a 0.1M aqueous solution of sodium hydrogen carbonate (containing 0.5M of sodium chloride, pH 8.4). Thus, the carrier for affinity chromatography, containing the terminal fucose-binding substance can be produced.

According to the chromatography utilizing the above described carrier for affinity chromatography containing the terminal fucose-binding substance, the desired GRA can be caught on the column by being bound to the terminal fucose-binding substance in the above described carrier. Then the GRA is obtained by carrying out an exchange reaction by passing a substance capable of binding the terminal fucose-binding substance through the column or by passing an adsorptive separator (eluent) such as a salt solution having a high concentration, an aqueous solution of potassium thiocyanate, a boric acid buffer solution or a hydrochloric acid-glycine buffer solution (pH 2.7), etc. through the column to separate the GRA.

Substances capable of binding the terminal fucose-binding substance to be used in the above mentioned exchange-reaction include, for example, fucose and terminal fucose-containing disaccharides and oligosaccharides.

The GRA obtained as described above according to the present invention contains glycoproteins having a terminal fucose glycosidic linkage structure. This GRA, if necessary, can further be purified or lyophilized by a conventional method. For example, this may be treated with a lectin capable of binding a terminal galactose and/or a terminal N-acetylgalactosamine, so as to isolate the GRA in the form as bound to said lectin.

Further, the process of the present invention can also be used as a means for purifying GRA previously obtained using the GRA as a starting material in place of cancer cell membrane components. This embodiment is also included in the scope of the present invention.

As mentioned above, the GRA obtained according to the present invention has a very high immunogenicity that causes an immune response specific to the cancer cells, and exhibits an excellent effect in the treatment and prevention of cancers.

In addition, the present invention provides a process for producing a thermally denatured antigen obtained by heat treatment of said GRA (hereinafter referred to as "thermally denatured GRA").

The thermally denatured GRA has a characteristic that may prevent the occurrence of humoral immunity of cancer-carrying hosts (low antibody productivity) and may bring about strong cell mediated immunity which is specific to cancer cells.

In general, it has been known that, since the immune reaction to cancers (tumor rejection) is based chiefly on cell mediated immunity, while humoral immunity, which is caused by an antibody to a cancer associated antigen by masking the antigen, and, by acting as an inhibitory factor for the immune reaction (blocking antibody) by itself or by forming an immune complex, or by changing the distribution of the antigen (antigenic modulation), sometimes results in not only the destruction of the immunological surveillance mechanism of the living body but also the acceleration of the growth of tumors to bring a disadvantageous action for the host. Therefore, the thermally denatured GRA as having the above mentioned characteristics is highly preferred as a preventive or a remedy for cancers. In addition, this can be used for the therapy and prophylaxis for cancers in a wide dosage range since the effect thereof has a low dependence on the concentration thereof.

Thermal treatment of the GRA is carried out under such conventional heating condition that may denature the protein component therein but not the glycosidic linkage therein. For example, it is carried out by heating the GRA in a solvent such as water, physiological saline or a phosphoric acid buffer solution at about 60° to 120° C., preferably 90° to 110° C. for 5 to 60 minutes, preferably 10 to 20 minutes.

The thermally denatured GRA prepared according to the process of the present invention is a glycoprotein composed of non-denatured glycosidic linkage structure moiety and thermally denatured protein moiety.

When lymphocytes are sensitized with the GRA or the thermally denatured GRA obtained according to the process of the present invention, killer cells are produced.

The lymphocytes used herein are not especially restricted, and any of normal or cancer-carrying lymphocytes of human or animal can be used. Examples of them include those derived from peripheral blood, bone marrow, lymph node, spleen, tonsil and thymus gland, etc. These lymphocytes can be isolated by, for example, a physical or chemical process or a surface membrane process, and they can be used for the process for producing killer cells.

Sensitization of lymphocytes with the GRA or thermally denatured GRA can be carried out by cultivating the lymphocytes in a medium containing the GRA or thermally denatured GRA for several hours to 10 days, preferably 1 to 5 days.

Various kinds of medium conventionally used for incubating this kind of cells can be used. It is preferred to use, for example, medium RPMI-1640 and medium Eagle MEM to which human serum, fetus calf serum (FCS), calf serum or horse serum, etc. is added. The GRA or the thermally denatured GRA to be added to the medium is preferred to be in an amount of 0.1–2000 ng/ml, preferably 1–1,000 ng/ml as a protein based on the $1 \times 10^6$ lymphocytes/ml.

Incubation is carried out, for example, at a temperature of 37° C. and pH of 7.2 or so according to the conventional method.

Thus resultant killer cells can multiply without any restriction in the above described medium containing T-cell growth factor (TCGF, IL-2). In this case, selective incubation of cloning of killer cells may be carried out by a conventional limiting dilution method. The killer cells can be stably preserved for a long period of time, if they are preserved in, for example, liquid nitrogen.

The resultant killer cells are substantially normal lymphocytes, which are characterized in that they have a cytotoxic activity specific to GRA.

The GRA and the thermally denatured GRA prepared according to the process of the present invention as described above are useful as an anticancer agent. The GRA and the thermally denatured GRA may be used alone as an active ingredient or they may be used together with other antimicrobial agents and/or anticancer agents. The anticancer agent containing the GRA or thermally denatured GRA prepared according to the process of the present invention as an active ingredient may have any form, if it contains an effective amount of the GRA or thermally denatured GRA as a main agent. In general, it is administered by intravenous injection, subcutaneous injection or intramuscular injection as a state of liposome-inclusion, a solution, a suspension or an emulsion, etc. In particular, the form of a liposome-inclusion is preferred. It can be provided as a dried state which can be liquefied by adding a suitable carrier before using. Such liquid agents may contain suspending agents such as methyl cellulose, emulsifiers such as lecithin, antiseptics such as methyl p-hydroxybenzoate and stabilizers or buffers which do not have an adverse influence upon an immune function of human and animal, etc. It is possible to use physiological saline as an aqueous medium and vegetable oils such as sesame oil, etc., mineral oils such as paraffin, etc., vegetable and animal oils such as squalene, etc., and propylene glycol, etc. as a non-aqueous medium. Further, such a liquid agent may contain suitable adjuvants for promoting immunity, such as, for example, Freund's complete adjuvant, saponin for animal and aluminum hydroxide for human, etc.

The above described anticancer agent can be administered to cancer patients one time or several times over a long period of time in order to remedy, and it can be administered to persons who are in danger of developing a cancer in order to prevent development of the cancer.

Since both the GRA and the thermally denatured GRA have low toxicity such that $LD_{50}$ (mouse, intraperitoneal) is 500 mg/kg or more as saccharide, they can be administered in an amount of a wide range. Accordingly, the amount of the GRA or thermally denatured GRA in the anticancer agent is not especially restricted, and it is generally preferred to be in a range of 0.001–100 μg/ml as saccharide. The amount of administration depends upon the state of malady, age and sex, and it is preferred to administer it one time to several times in an amount of 0.001–1,000 μg/kg/day.

Further, killer cells obtained as described above are useful as an anticancer agent, too. Such an anticancer agent is preferred to be used as an injection together with a carrier used for this kind of blood agent. The carrier is not specifically restricted, and it is preferred to use those which are isotonic to blood, preferably physiological saline. In carrying out production of the agent, it is preferred that, after the killer cells are washed sufficiently with physiological saline to remove the above described medium, they are suspended in a carrier.

The concentration of killer cells in the above described agent is not especially restricted, and it is generally preferred in a range of $10^5$ to $10^9$ cells/ml. Further, toxicity of killer cells is not observed when they are administered in an amount of $10^8$ cells/mouse (intraperitoneal). The amount of administration depends upon the state of malady, age and sex, but it is preferred to administer one time to several times in an amount of $10^5$ to $10^{12}$ cells/kg/day.

In the following, the present invention is illustrated with reference to examples, reference examples and reference tests, but the present invention is not limited to them.

The cancer cells used hereunder are all known and have been obtained from Laboratory of Niigata University (Dr. Suzuki, assistant professor) and from Japan Immunoresearch Laboratories Co., Ltd.

REFERENCE EXAMPLE 1

Using GRA 2 described in GB No. 2106935A in an amount of 5 μg as protein together with a Freund's complete adjuvant, a Balb/c mouse was subjected to immunization by subcutaneous administration at a rate of one time in two weeks. After 3 days from the third immunization, the spleen was taken out, and the spleen cells were washed three times with RPMI-1640 medium. Mouse myeloma cell line SP2 (refer to "Rinsho Meneki", Vol. 13, No. 11, pp. 912–919, 1981) was washed analogously, and the SP2 cells ($1 \times 10^7$ cells) and the above-mentioned spleen cells ($4 \times 10^7$ cells) were put in a centrifugal tube and blended therein. After centrifugation (200×g, 5 minutes), the supernatant was removed with a Pasteur pipet. 1 ml of an RPMI-1640 solution containing 45 w/v % of polyethylene glycol 4000 (produced by Sigma Co.) and kept warm at 37° C. was added dropwise thereto and gently blended for 2 minutes. 1 ml of an RPMI-1640 containing 15% FCS and 1 mM pyruvate (hereinafter referred to "complete RPMI-1640") and kept warm at 37° C. was added dropwise thereto and gently stirred for 1 minute, and then the same amount of said complete RPMI-1640 and thereafter 8 ml thereof was further added dropwise thereto and each gently stirred for 1 minutes and 2 minutes, respectively. After the resulting mixture was subjected to centrifugation (200×g, 5 minutes), the supernatant was removed off, and the remaining content was suspended in the complete RPMI-1640 kept warm at 37° C. in an amount of $1 \times 10^7$ cells/ml. Each 100 μl of the obtained suspension was inoculated in a Microtest-II plate (produced by Falcon Co.) and cultured in an incubator containing 5% $CO_2$, at 37° C. After 24 hours, 100 μl of the above-mentioned complete RPMI-1640 containing $1.0 \times 10^{-4}$M hypoxanthine, $4.0 \times 10^{-7}$M aminopterin and $1.6 \times 10^{-5}$M thymidine (hereinafter referred to as "HAT medium") was added to each well. Afterwards, a half of the supernatant in each well was exchanged for a fresh HAT medium in every 2nd, 3rd, 5th, 8th and 11th day, and in the 14th day, a half of the supernatant was analogously exchanged for a complete RPMI-1640 containing $1.0 \times 10^{-4}$M hypoxanthine and $1.6 \times 10^{-5}$M thymidine (hereinafter referred to as HT medium"). In the same manner, a half of the supernatant was exchanged for a fresh HT medium in evey 18th, 22nd, 25th and 26th day, and in the 28th day, a half of the supernatant was exchanged for a fresh complete RPMI-1640. Afterwards, the proliferation was kept carried out in this complete RPMI-1640. The thus obtained hybridoma was cloned by means of a limiting dilution-culture method. More precisely, the complete RPMI-1640 medium was adjusted to contain hybridomas in an amount of 3 cells/ml and Balb/c mouse thymus cells in an amount of $1 \times 10^7$ cells/ml, and this was implanted in a plate having 96 wells each in an amount of 0.2 ml/well and cultured therein. The proliferated hybridoma was further cloned analogously. For the check of the clone which may produce the desire antibody, was used a 96-well plate (produced by Dynatech Labortory Co.) coated with 10 ng/well of a purified $III^3FucnLc_4$, $III^3V^3Fuc_2nLc_6$ or $III^3V^3VII^3Fuc_3nLc_8$, 30 ng/well of cholesterol and 50 ng/well of lecithin in a solid phase method using a rabbit antimouse immunoglobulin (produced by Kappel Co.) and $^{125}$I-Protein A (produced by Sigma Co.). Thus, the desired hybridoma represented by clone No. GGF was obtained.

(2) The hybridoma of clone No. GGF as obtained in the above (1) was cultured in a complete RPMI-1640 medium put in an incubator containing 5% $CO_2$, at 37° C. for 48 hours. The cultured solution was subjected to centrifugal separation (3,000 rpm, 10 minutes), to obtain a cultured supernatant containing a monoclonal antibody (hereinafter referred to as "GGF").

(3) $1 \times 10^6$ hybridoma cells of the clone No. GGF as obtained in the above (1) were suspended in 0.5 ml of RPMI-1640 medium and intraperitoneally administered to Balb/c mouse. After 2 to 3 weeks, the accumulated ascites was taken out, and thus 2 to 5 ml/mouse of an ascites containing an antibody GGF was obtained. The antibody concentration was about 0.5 mg/ml.

(4) Immunoglobulin Class

The classification was carried out according to a method of Yeh et al., using a rabbit antibody to the corresponding kind of mouse immunoglobulin class (Litton. Bionetico. Inc. Kensington, Md. 20795) and $^{125}$I-labeled Protein A (Ming-Yang Yeh et al. *Proc. Natl. Acad. Sci.* U.S.A. vol. 76, No. 6, pp. 2927-2931, 1979). In the result, the GGF was proved to belong to an IgG 3 subclass.

(5) Reactivity of the Antibody GGF to Various Kinds of Glycolipid Antigens (a) As a purified antigen was used $III^3FucnLc_4$, $III^3V^3Fuc_2nLc_6$ or $III^3V^3VII^3Fuc_3nLc_8$ (*Biochem. Biophys. Res. Commun.*, 109, (1), pp. 36-44, 1982). The antibody obtained in the above (2) (and step-wise diluted samples thereof) were reacted with said antigen in 10 ng/well of a vinyl strip (produced by Coster Co.) coated with cholesterol (30 ng/well) and lecithin (50 ng/well).

After well washed with PBS, the antibody bound to the purified antigen was measured, using a rabbit antimouse immunoglobulin as a second antibody and then $^{125}$I-protein A. The binding ratio was calculated on the basis of the radiation count. In the result, the antibody GGF was proved to have a reactivity with $III^3V^3Fuc_2nLc_6$ and $III^3V^3VII^3Fuc_3nLc_8$, but this did not react with $III^3FucnLc_4$.

(b) Influence of addition of monosaccharide on the first reaction of lectin-GGF binding assay According to a method as explained below, an influence on the first reaction (reaction of monoclonal antibody and GRA 2) of the lectin-GGF binding assay in the case that a monosaccharide was added thereto, was investigated. The result is given in the FIGURE. In this connection, it was noticed that the binding was inhibited in every case where $III^3V^3Fuc_2nLc_6$ or $III^3V^3VII^3Fuc_3nLc_8$ was used instead of the monosaccharide.

Measuring Method:

(1) Each one of polystyrene beads coated with the monoclonal antibody GGF was put in every assay tube.

(2) 0.1 ml of GRA 2 solution and saccharide (saccharide concentration: fucose (600 μg) and galactose (6 mg)) were put in each assay tube.

(3) In addition, 0.6 ml of 10 mM phosphoric acid buffer (pH 7.0) containing 1 mM-$MgCl_2$, 0.1% HSA and 0.1 M-NaCl was added thereto.

(4) After blended, these were incubated at room temperature for 3 hours and then at 4° C. for 24 hours.

(5) Each bead was washed five times with a washing buffer containing:
0.05M tris-HCl buffer (pH 7.2)
2 mM-$CaCl_2$
2 mM-$MgCl_2$
0.85% NaCl (6) Then, 0.5 ml of the washing buffer and 0.1 ml of PNA-POX solution were added to each assay tube and blended therein.

(7) These were incubated at room temperature for 2 hours and then at 4° C. for 18 hours.

(8) These were washed five times with 0.85% common salt solution.

(9) Each bead was transferred to a new assay tube, and 2 ml of 0.85% common salt solution and 0.5 ml of 3 mg/ml ortho-phenylenediamine solution(dissolved in citric acid buffer of pH 5.8) containing 0.03% (final concentration) of hydrogen peroxide were added thereto.

(10) After blended, these were incubated at room temperature for 30 minutes.

(11) 1 ml of 3N-HCl was added and the reaction was terminated.

(12) Using a spectrophotometer was measured the absorbance of a wavelength of 492 nm in each sample.

(c) Reactivity to various kinds of human cells:

Cells fixed on a plate were treated with a 5% bovine serum albumin-containing phosphoric acid buffer saline solution (pH 7.4) for one hour, and then antibody GGF (100 time-diluted antibody obtained in the above mentioned (3)) was added thereto and incubated for 18 hours. Then, the cells on the plate were treated with an FITC-labeled rabbit antibody (produced by JIMRO Co.) capable of reacting with a mouse IgG 3, as a second antibody, said antibody having been diluted 1000 times.

The results are given in the following Table 1, where "positivity" is a percentage of dyed cells.

TABLE 1

| Cancer | Cell Line | Positivity (%) |
|---|---|---|
| Lymphoma | MOLT-4 | 50.0 |
|  | K-562 | 97.1 |
| Stomach | KATO-III | 37.3 |
| Cancer | MKN-74 | 80.6 |
| Lung | PC-3 | 82.1 |
| Cancer | QG-90 | 4.2 |
| Renal | NRC-125 | 8.3 |
| Cancer |  |  |

REFERENCE EXAMPLE 2

(1) After 3 g of CNBr-activated Sepharose 4B (produced by Pharmacia Co.) was sufficiently washed with 1 mM-HCl, it was suspended in 200 ml of 0.1M sodium hydrogen carbonate (pH=8.5). 5 ml of a 0.01M phosphate buffer solution (pH=7.7) containing 20 mg of *Lotus tetragonolobus* lectin was added thereto and the reaction was carried out at 25° C. for 2 hours with stirring at times to obtain insolubilized lectin (*Lotus tetragonolobus* lectin)-Sepharose.

(2) To 2 ml of Antibody GGF obtained in Reference Example 1-(2), a 0.1M aqueous solution of sodium hydrogen carbonate containing 5 g/15 ml of Bromocyan Sepharose (Pharmacia Co.) and 0.5M of NaCl (pH=8.3) was added, and the resultant mixture was stirred for 2 hours to obtain an insolubilized antibody (GGF-Sepharose).

EXAMPLE 1

(1) About 5 g (wet weight) of KATO-III cells were homogenized in 50 ml of PBS by means of a mill (Waring Blender). The precipitate obtained by centrifugal separation (100,000×g, 1 hour) was added to 50 ml of a 0.01M tris-hydrochloric acid buffer solution (pH 7.6) containing 2% of Triton X-100, 2 mM of $MgCl_2$, 2 mM of $CaCl_2$ and 0.85% of NaCl, while stirred. The supernatant obtained by centrifugal separation (100,000×g, 1 hour) was brought into a column ($\phi$0.8×15 cm) of an insolubilized lectin (carrier obtained in the above mentioned Reference Example 2-(1)) equilibrated with a 0.01M tris-hydrochloric acid buffer solution (pH 7.6) containing 0.015% of Triton X-100, 2 mM of $MgCl_2$, 2 mM of $CaCl_2$ and 0.85% of NaCl. After washing with the same buffer solution, elution was carried out with the same buffer solution but containing 0.1M of fucose, and the eluate was dialyzed with a 0.85% aqueous solution of NaCl (5 liters×3, two days). After concentrated (CX-10 ultrafilter: Millipore Co.), this was filtered (0.2 $\mu$m filter: Amicon Co.), to obtain a GRA solution. The amount of protein: 1.5 mg. The amount of saccharide: 1.6 mg. This is called "TCA-1".

(2) In the above-mentioned procedure (1), about 10 g of QG-90 cells were used instead of the KATO-III cells, and a column of an insolubilized antibody obtained in the above mentioned Reference Example 2-(2) (eluent: 0.2M hydrochloric acid-glycine buffer solution, pH of 2.7) was used as a carrier, and treated analogously, to obtain a GRA solution. The amount of protein: 570 $\mu$g. The amount of saccharide: 500 $\mu$g. This is called "TCA-2".

(3) A column of an insolubilized antibody obtained in the above-mentioned Reference Example 2-(2) was washed with a 0.01M tris-hydrochloric acid buffer solution (pH=7.6) containing 0.015% of Triton X-100, 2 mM of $MgCl_2$, 2 mM of $CaCl_2$ and 0.85% of NaCl, and then GRA-1 described in GB 2106935A was applied thereto, in an amount of 300 $\mu$g as protein. After washed with the same buffer solution, this was eluted with a 0.2M hydrochloric acid-glycine buffer solution (pH=2.7), to obtain a GRA solution. The amount of protein: 200 $\mu$g. The amount of saccharide: 220 $\mu$g. This is called "TCA-3".

(4) In the above procedure (3), GRA-8 described in GB No. 2106935A was used instead of the GRA-1, the amount of said GRA-8 used being 20 $\mu$g as protein, and treated analogously, to obtain a GRA solution. The amount of protein: 15 $\mu$g. The amount of saccharide: 13 $\mu$g. this is called "TCA-4".

EXAMPLE 2

(1) A physiological saline solution containing TCA-1, in an amount of 100 $\mu$g as protein, obtained in the above mentioned Example 1-(1) was heated in a hot-water bath at 100° C. for 10 minutes to obtain a thermally denatured GRA. This is called "TCA-1H".

(2) In the above procedure (1), each of TCA-2 to 4 was used instead of the TCA-1 and treated analogously, to obtain each thermally denatured GRA given in the following Table 2.

TABLE 2

| Raw Material | Heating Condition | Thermally Denatured GRA |
| --- | --- | --- |
| TCA-2 | 100° C., 10 min. | TCA-2H |
| TCA-3 | 120° C., 5 min. | TCA-3H |
| TCA-4 | 100° C., 10 min. | TCA-4H |

REFERENCE TEST 1

(1) Peripheral blood lymphocytes obtained from a healthy adult human by centrifugal separation by means of Ficollpack (Pharmacia Co.) were controlled with a medium RPMI-1640 containing 10% of FCS so as to be $1.5\times10^6$ cells/ml. To 10 ml of it, TCA-2 was added so as to have an amount of protein of 25 ng/ml, and incubation was carried out at 37° C. in carbonic acid gas incubator for 48 hours to obtain killer cells.

Apart from this, killer cells were obtained likewise, but with no addition of TCA (control).

(2) After killer cells obtained in the above (1) were washed twice with the medium RPMI-1640 (1000 rpm, 10 minutes), they were controlled with the same medium containing 10% of FCS so as to be $1.5\times10^6$ cells/ml, which was called Effector cell (E). As target cells (T), those which were obtained by controlling Daudi washed twice with the above described medium with the same medium containing 10% of FCS so as to be $1.5\times10^6$ cells/ml were used.

100 $\mu$l of the above described E and 100 $\mu$l of the T were blended. After the mixture was incubated at 37° C. for 1 hour, a test tube containing the mixture was put in iced water to stop the reaction, and the number of survival cells was measured by carrying out deying with 0.2% Trypan Blue. The killer activity of E was calculated from the following formula.

Killer Activity (%)=[(number of cells in case of using E of the control) - (number of cells tested)]/(E'+,T')

wherein E' represents the number of survival cells after 100 $\mu$l of E is incubated at 37° C. for 1 hour; and T' represents the number of survival cells after 100 $\mu$l of T is incubated at 37° C. for 1 hour.

In the result, 20.5% of the killer activity of E in average was admitted.

(3) Analogously to the above mentioned (1) and (2), the killer activity of killer cells derived from each of TCA-1, TCA-3, TCA-4, TCA-1H, TCA-2H, TCA-3H, and TCA-4H was calculated, and as a result, nearly the same activity as in the above was observed in every case.

REFERENCE TEST 2

(1) TCA-3H obtained in Example 2 was controlled with physiological saline so as to have an amount of protein of 100 ng/ml. This is called Anticancer agent No. 1.

(2) $1\times10^4$ cells of LLC derived from C57BL/6 mouse (Charles liver, male, 5W) were injected to said C57BL/6 mouse from a vein of the tail thereof. After 6 days from the injection, the above described Anticancer agent No. 1 was administered to said mouse in an amount of 1 ml/mouse day from a vein of the tail thereof for 3 days continuously. After 22 days from the injection of LLC cells, the lung was picked up and presence or absence of implanted LLC on the lung was visually observed and the weight of the lung was measured. As controls, a group to which the anticancer agent was not administered and normal mice were used. Results are shown in Table 3.

TABLE 3

| Group | Number of Tested Mice (n) | Average Weight of Lung (g) | Presence or Absence of Implantation |
|---|---|---|---|
| Control | 5 | 0.351 | + |
| TCA | 5 | 0.195 | − |
| Normal | 5 | 0.177 | − |

It is confirmed from the Table 3 that administration of the thermally denatured antigen of the present invention clearly causes tumor rejection or suppression of tumor growth.

While the invention has been described in detail and with reference to specific embodiments thereof, it will be apparent to one skilled in the art that various changes and modifications can be made therein without departing from the spirit and scope thereof.

What is claimed is:

1. A process for preparing a thermally denatured, cancer cell-derived glycosidic linkage related antigen, comprising treating a cell membrane component of cancer cells with an antibody capable of binding a terminal fucose glycosidic linkage structure, isolating the glycosidic linkage related antigen and heating the glycosidic linkage related antigen such that the protein moiety in said glycosidic linkage related antigen is denatured but the glycosidic linkage moiety in said glycosidic linkage related antigen is not denatured, wherein said antibody is a monoclonal antibody which reacts with $III^3V^3Fuc_2nLc_6$ and $III^3V^3VII^3Fuc_3nLc_8$ but does not react with $III^3FucnLc_4$.

2. A process for preparing a thermally denatured, cancer cell-derived glycosidic linkage related antigen, comprising treating a cell membrane component of cancer cells with a lectin capable of binding a terminal fucose glycosidic linkage structure, isolating the glycosidic linkage related antigen and heating the glycosidic linkage related antigen such that the protein moiety in said glycosidic linkage related antigen is denatured but the glycosidic linkage moiety in said glycosidic linkage related antigen is not denatured, wherein said process comprises the steps of:
    (a) homogenizing human cancer cells and collecting a precipitate;
    (b) solubilizing the precipicate and collecting a resultant supernatant;
    (c) reacting the supernantant with said lectin which is Lotus tetragonolobus lectin to bind the glycosidic linkage related antigen;
    (d) collecting the bound glycosidic linkage related antigen, releasing the glycosidic linkage related antigen from the lectin and isolating the released glycosidic linkage related antigen; and
    (e) heating the glycosidic linkage related antigen at 90° to 110° C. for 5 to 60 minutes.

3. A process for preparing a thermally denatured, cancer cell-derived glycosidic linkage related antigen, comprising treating a cell membrane component of cancer cells with an antibody capable of binding a terminal fucose glycosidic linkage structure, isolating the glycosidic linkage related antigen and heating the glycosidic linkage related antigen such that the protein moiety in said glycosidic linkage related antigen is denatured but the glycosidic linkage moiety in said glycosidic linkage related antigen is not denatured, wherein said process comprises the steps of:
    (a) homogenizing human cancer cells and collecting a precipitate;
    (b) solubilizing the precipicate and collecting a resultant supernatant;
    (c) reacting the supernantant with said antibody which is a monoclonal antibody which reacts with $III^3V^3Fuc_2nLc_6$ and $III^3V^3VII^3Fuc_3nLc_8$ but does react with $III^3FucnLc_4$ to bind the glycosidic linkage related antigen;
    (d) collecting the bound glycosidic linkage related antigen, releasing the glycosidic linkage related antigen from the monoclonal antibody and isolating the released glycosidic linkage related antigen; and
    (e) heating the glycosidic linkage related antigen at 90° to 100° C. for 5 to 60 minutes.

* * * * *